(12) United States Patent
Dehghan Marvast et al.

(10) Patent No.: US 10,549,123 B2
(45) Date of Patent: Feb. 4, 2020

(54) ASSISTING APPARATUS FOR ASSISTING IN PERFORMING A BRACHYTHERAPY

(71) Applicant: KONINKLIJKE PHILIPS N.V., Eindhoven (NL)

(72) Inventors: Ehsan Dehghan Marvast, New York, NY (US); Amir Mohammad Tahmasebi Maraghoosh, Ridgefield, CT (US); Shyam Bharat, Cortlandt Manor, NY (US); Sandeep M. Dalal, Cortlandt Manor, NY (US); Cynthia Ming-fu Kung, New York, NY (US); Jochen Kruecker, Washington, DC (US)

(73) Assignee: Koninklijke Philips N.V., Eindhoven (NL)

( * ) Notice: Subject to any disclaimer, the term of this patent is extended or adjusted under 35 U.S.C. 154(b) by 833 days.

(21) Appl. No.: 14/646,408

(22) PCT Filed: Nov. 8, 2013

(86) PCT No.: PCT/IB2013/059989
§ 371 (c)(1),
(2) Date: May 21, 2015

(87) PCT Pub. No.: WO2014/091330
PCT Pub. Date: Jun. 19, 2014

(65) Prior Publication Data
US 2015/0306426 A1    Oct. 29, 2015

Related U.S. Application Data

(60) Provisional application No. 61/735,669, filed on Dec. 11, 2012.

(51) Int. Cl.
*A61N 5/10* (2006.01)
*A61B 8/08* (2006.01)

(52) U.S. Cl.
CPC .......... *A61N 5/1071* (2013.01); *A61B 8/0833* (2013.01); *A61N 5/1007* (2013.01);
(Continued)

(58) Field of Classification Search
CPC .. A61N 5/1001; A61N 5/1002; A61N 5/1007; A61N 5/103; A61N 5/1037; A61N 5/1038; A61N 5/1049; A61N 5/1071
See application file for complete search history.

(56) References Cited

U.S. PATENT DOCUMENTS 6,471,710 B1 * 10/2002 Bucholtz .............. G01B 11/005
600/229
6,610,013 B1    8/2003 Downey et al.
(Continued)

FOREIGN PATENT DOCUMENTS

CN    201483492 U    5/2010

OTHER PUBLICATIONS

Pennee, X. et al. "Understanding the "Demon's Algorithm": 3D Non-rigid Registration by Gradient Descent", Medical Image Computing and Computer-Assisted Intervention—MICCAI'99, pp. 597 to 606 (1999).

(Continued)

*Primary Examiner* — Carrie R Dorna

(57) ABSTRACT

The invention relates to an assisting apparatus for assisting in performing brachytherapy. The position of an introduction element (17) like a catheter is tracked particularly by using electromagnetic tracking, while a group of seeds is introduced into a living object (2). This provides a rough knowledge about the position of the seeds within the object. An ultrasound image showing the group is generated depending on the tracked position of the introduction element and, thus, depending on the rough knowledge about the position of the seeds, in order to optimize the ultrasound visualization with (Continued)

respect to showing the introduced seeds. Based on this optimized ultrasound visualization the position of a seed of the group is determined, thereby allowing for an improved determination of seed positions and correspondingly for an improved brachytherapy performed based on the determined positions.

14 Claims, 8 Drawing Sheets

(52) U.S. Cl.
CPC ............... *A61N 2005/1012* (2013.01); *A61N 2005/1024* (2013.01); *A61N 2005/1074* (2013.01)

(56) References Cited

U.S. PATENT DOCUMENTS

| | | |
|---|---|---|
| 2003/0065260 A1 | 4/2003 | Cheng et al. |
| 2008/0212857 A1 | 9/2008 | Pfister et al. |
| 2009/0198094 A1* | 8/2009 | Fenster ............... A61B 8/0833 600/3 |
| 2010/0312038 A1 | 12/2010 | Schechter |
| 2011/0172526 A1 | 7/2011 | Falco et al. |
| 2012/0243759 A1 | 9/2012 | Fujisawa et al. |
| 2013/0102891 A1 | 4/2013 | Binnekamp et al. |
| 2014/0187919 A1 | 7/2014 | Parthasarathy et al. |
| 2015/0375013 A1 | 12/2015 | Lachaime et al. |

OTHER PUBLICATIONS

Welch, E.B. et al., "Interscan Registration Using Navigator Echoes", Magnetic Resonance in Medicine 52:1448-1452 (2004).

* cited by examiner

ASSISTING APPARATUS FOR ASSISTING IN PERFORMING A BRACHYTHERAPY

CROSS-REFERENCE TO PRIOR APPLICATIONS

This application is the U.S. National Phase application under 35 U.S.C. § 371 of International Application Serial No. PCT/IB2013/059989, filed on Nov. 8, 2013, which claims the benefit of United States application Ser. No. 61/735,669, filed on Dec. 11, 2012. These applications are hereby incorporated by reference herein.

FIELD OF THE INVENTION

The invention relates to an assisting apparatus, an assisting method and an assisting computer program for assisting in performing a brachytherapy. The invention relates further to a brachytherapy system comprising the assisting apparatus.

BACKGROUND OF THE INVENTION

US 2009/0198094 A1 discloses an apparatus for determining a distribution of a selected therapy in a target volume. The apparatus comprises a three-dimensional ultrasound transducer for capturing volume data from the target volume and a computing device in communication with the three-dimensional ultrasound transducer for receiving the volume data. The computing device is further adapted to determine the distribution of the selected therapy in the target volume along a set of planned needle trajectories using the volume data, wherein at least one of the needle trajectories is oblique to at least one other of the planned needle trajectories. The quality of the ultrasound imaging may be reduced, which in turn may lead to a reduced accuracy of the determination of the distribution of the selected therapy in the target volume. If a brachytherapy is based on this determined distribution having a reduced accuracy, also the quality of the brachytherapy is reduced.

SUMMARY OF THE INVENTION

It is an object of the present invention to provide an assisting apparatus, an assisting method and an assisting computer program for assisting in performing brachytherapy, which allow for an improved quality of the brachytherapy. It is a further object of the present invention to provide a brachytherapy system for applying a brachytherapy to a living object, wherein the brachytherapy system comprises the assisting apparatus.

In a first aspect of the present invention an assisting apparatus for assisting in performing brachytherapy is presented, during which a brachytherapy seed group including at least one brachytherapy seed is introduced into a living object by using an introduction element, the apparatus comprising:
  a tracking unit for tracking the position of the introduction element during the introduction of the group into the living object,
  an ultrasound unit for generating an ultrasound image of the living object, wherein the ultrasound image shows the group within the living object, wherein the generation of the ultrasound image is controlled depending on the tracked position of the introduction element, and
  a seed position determining unit for determining the position of a brachytherapy seed of the group depending on the generated ultrasound image.

Since the tracking unit tracks the position of the introduction element during the introduction of the group into the living object, it is already roughly known where the respective group of brachytherapy seeds has been placed within the living object. This rough knowledge about the position of the seeds within the living object can be used by the ultrasound unit for optimizing the ultrasound imaging for imaging in this roughly known region of the living object, thereby allowing for an improvement of the ultrasound visualization. Since the position of the brachytherapy seed of the group is determined based on the ultrasound image obtained by the improved ultrasound visualization, also the determination of the position of the brachytherapy seed can be performed with improved accuracy. This in turn allows for an improved quality of a brachytherapy, which is based on the determined position of the brachytherapy seed.

The group of at least one brachytherapy seed can comprise one or several brachytherapy seeds. The living object is preferentially a human being or an animal. The brachytherapy is preferentially a low dose rate (LDR) brachytherapy, which is especially adapted for treating a prostate.

The tracking unit is preferentially adapted to electromagnetically track the position of the introduction element during the introduction of the group into the living object. Moreover, the tracking unit can be used to globally or roughly find a target region with introduced seeds, wherein then an ultrasound beam can be directed to this globally or roughly found target region.

It is preferred that the ultrasound unit is adapted to generate an ultrasound image, before the group is introduced into the living object, and an actual ultrasound image, after the group has been introduced into the living object, wherein the seed position determining unit is adapted to register the ultrasound images with respect to each other, to generate a subtraction image by subtracting the registered ultrasound images from each other and to determine the position of a brachytherapy seed of the group depending on the generated subtraction image. The registration is preferentially a deformable registration.

The ultrasound image, which has been generated before the group is introduced into the living object, can be a base ultrasound image, which has been generated, before any brachytherapy seed has been introduced into the living object. In this case the positions of all brachytherapy seeds, which have already been introduced into the living object, can be determined directly from the subtraction image. However, if several groups of brachytherapy seeds are consecutively introduced into the living object by using the introduction element, wherein each group includes at least one brachytherapy seed, for each group of brachytherapy seeds an actual ultrasound image can be generated, after the respective group has been introduced into the living object, and a previous ultrasound image can be generated, before the respective group has been introduced into the living object and after the previous group of brachytherapy seeds has been introduced into the living object. The kind of imaging may be called "incremental imaging". For each group of brachytherapy seeds a subtraction image can be generated by subtracting the respective actual and previous ultrasound images from each other, wherein the respective subtraction image can be used for determining the positions of the one or several brachytherapy seeds of the respective group. Since this determination of the positions of the brachytherapy seed is performed for each group that have already been introduced into the living object, the positions of all brachytherapy seeds introduced into the living object can be determined by incremental imaging.

Generally, an ultrasound image may comprise bright image artifacts, which can be caused by microcalcifications in the living object and which may be misclassified as being brachytherapy seeds. These bright image artifacts are supposed to be present in subsequent images such that, if these images are subtracted from each other, the resulting subtraction image should not comprise these bright image artifacts. By determining the positions of the brachytherapy seeds based on the subtraction images the likelihood of a misclassification, i.e. the determination of a supposed seed position which in fact is, for instance, a microcalcification position, can therefore be reduced, thereby further improving the quality of determining the positions of the brachytherapy seeds and, thus, the quality of the brachytherapy, which is based on these determined positions.

It is further preferred that several groups of brachytherapy seeds are consecutively introduced into the living object by using the introduction element, wherein each group includes at least one brachytherapy seed, wherein the ultrasound unit is adapted to generate an actual ultrasound image, after a group has been introduced into the living object, wherein the seed position determining unit is adapted to determine the positions of brachytherapy seeds of groups already introduced into the living object depending on the generated actual ultrasound image, in order to allow for an introduction of further groups depending on the positions of the brachytherapy seeds of groups already introduced. In particular, the seed position determining unit can be adapted to a) register the actual ultrasound image and a previous ultrasound image, which has been acquired after a previous group and before the actual group has been introduced, with respect to each other, b) generate a subtraction image by subtracting the registered ultrasound images from each other, c) determine the positions of the brachytherapy seeds of the actually introduced group depending on the subtraction image, d) provide the positions of the brachytherapy seeds of groups having been introduced into the living object before the actual group has been introduced, and e) combine the actually determined positions and the provided positions for determining the positions of all groups already introduced into the living object. This allows considering modifications in the positions of the already introduced brachytherapy seeds, which may be caused by a swelling of the living object, for instance, of the prostate, while introducing the further brachytherapy seeds, thereby allowing for a further improved quality of the brachytherapy.

In a preferred embodiment the apparatus further comprises a region of interest determining unit for determining a region of interest to be treated within the living object depending on the generated actual ultrasound image, in order to allow for an introduction of further groups also depending on the region of interest determined depending on the actual ultrasound image. The region of interest to be treated within the living object is, for instance, the prostate or a certain region within the prostate like a tumor region within the prostate. The region of interest determining unit can also be adapted to determine, i.e. segment, further elements of the living object, like vessels, organs, et cetera, based on the actual ultrasound image. The region of interest, i.e. the location and/or shape of the region of interest, and optionally further determined elements may change during the introduction of the several groups of brachytherapy seeds. Considering this possible change while introducing the several groups of brachytherapy seeds can further improve the accuracy of determining the positions of the brachytherapy seeds and, thus, the quality of the brachytherapy applied depending on the determined positions.

The apparatus preferentially further comprises a) a treatment plan providing unit for providing a treatment plan defining a spatial arrangement of brachytherapy seeds within the living object, wherein the introduction element is adapted to introduce the groups in accordance with the treatment plan, and b) a treatment plan updating unit for updating the treatment plan based on the determined positions of the brachytherapy seeds of the groups already introduced into the living object, wherein the introduction element is adapted to introduce further groups depending on the updated treatment plan. The treatment plan updating unit may be further adapted to update the treatment plan also based on the determined region of interest and optionally further elements of the living object, which may have been determined based on the actual ultrasound image.

The provided treatment plan depends preferentially on a region of interest and optionally on further elements of the living object like vessels, organs et cetera, which are shown in a base ultrasound image, wherein the region of interest should be treated by the brachytherapy seeds, wherein the base ultrasound image has been acquired, before any group of brachytherapy seeds has been introduced into the living object, wherein the region of interest determining unit is adapted to generate a registration transformation registering the base ultrasound image and the actual ultrasound image with respect to each other and to update the region of interest and the optional further elements shown in the base ultrasound image by using the registration transformation, and wherein the treatment plan updating unit is adapted to update the treatment plan based on the determined positions of the brachytherapy seeds of the groups already introduced into the living object, based on the updated region of interest and optionally also based on the updated further elements. It is therefore not necessarily required to segment the region of interest and the optional further elements in each actual ultrasound image, which may be acquired during incremental imaging, because the actual region of interest, i.e. the actual location and/or shape of the region of interest, and also the optional actual further elements can readily be determined by applying the registration transformation to the region of interest and the optional further elements initially determined in the base ultrasound image. For instance, in the base ultrasound image the region of interest and also further parts of the living object may be segmented for determining their locations and/or shapes within the living object, wherein to these segmentations the registration transformation can be applied, in order to provide updated segmentations, which can be used for updating the treatment plan.

The registration between the actual ultrasound image and the base ultrasound image can be a direct registration, i.e. each actual ultrasound image, which has been generated for the respective group, can be registered with the base ultrasound image, for generating for the respective group the registration transformation. However, also incremental registration can be used for finally obtaining a registration between the base ultrasound image and the actual ultrasound image of the respective group. That means the base ultrasound image can be registered with the actual ultrasound image of the first group, the actual ultrasound image of the first group can be registered with the actual ultrasound image of the second group, the actual ultrasound image of the second group can be registered with the actual ultrasound image of the third group, et cetera, in order to have the actual ultrasound images of each group registered with the base ultrasound image.

It is further preferred that the ultrasound unit is adapted to use a steerable ultrasound beam for generating the ultrasound image, wherein the ultrasound beam is controlled depending on the tracked position of the introduction element. Moreover, it is preferred that the ultrasound unit is adapted to generate a compound ultrasound image as the ultrasound image by acquiring several ultrasound images which correspond to different ultrasound beam directions and by combining the several ultrasound images. This allows providing an ultrasound image showing all brachytherapy seeds, which have already been introduced into the living object, even if in a certain ultrasound beam direction one or several brachytherapy seeds are not visible because of, for example, shading effects. This allows for a further improved accuracy of determining the positions of the brachytherapy seeds within the living object, which in turn leads to a further improved quality of the brachytherapy performed based on the determined positions.

In a further aspect of the present invention a brachytherapy system for applying brachytherapy to a living object is presented, wherein the brachytherapy system comprises:
  an introduction element for introducing several groups of brachytherapy seeds consecutively into the living object in accordance with the treatment plan, and
  an assisting apparatus for assisting in performing the brachytherapy as defined in claim 1.

In a further aspect of the present invention an assisting method for assisting in performing brachytherapy is presented, during which a brachytherapy seed group including at least one brachytherapy seed is introduced into a living object by using an introduction element, wherein the assisting method comprises:
  tracking the position of the introduction element during the introduction of the group into the living object by a tracking unit,
  generating an ultrasound image of the living object by an ultrasound unit, wherein the ultrasound image shows the group within the living object, wherein the generation of the ultrasound image is controlled depending on the tracked position of the introduction element, and
  determining the position of a brachytherapy seed of the group depending on the generated ultrasound image by a seed position determining unit.

In a further aspect of the present invention an assisting computer program for assisting in performing brachytherapy is presented, during which a brachytherapy seed group including at least one brachytherapy seed is introduced into a living object by using an introduction element, the assisting computer program comprising program code means for causing an assisting apparatus as defined in claim 1 to carry out the assisting method as defined in claim 12, when the computer program is run on a computer controlling the assisting apparatus.

It shall be understood that the assisting apparatus of claim 1, the brachytherapy system of claim 11, the assisting method of claim 12, and the assisting computer of claim 13 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
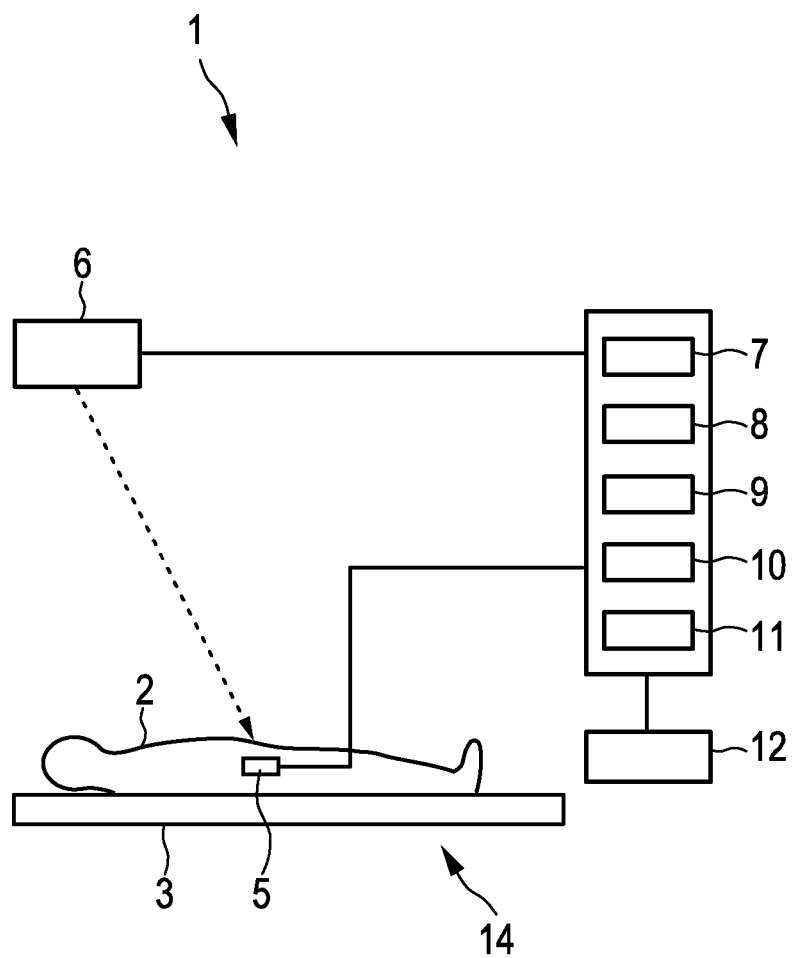
FIG. 1 shows schematically and exemplarily an embodiment of a brachytherapy system for applying brachytherapy to a person.

FIG. 1 shows schematically and exemplarily an embodiment of a brachytherapy system 14 for applying brachytherapy to a person 2 lying on a support means 3 like a table. The brachytherapy system 14 is adapted to perform a LDR brachytherapy, wherein several groups of brachytherapy seeds are consecutively introduced into the person 2 by using a placing unit 5. The placing unit 5 is schematically and exemplarily shown in more detail in FIG. 2.

Figure 2:
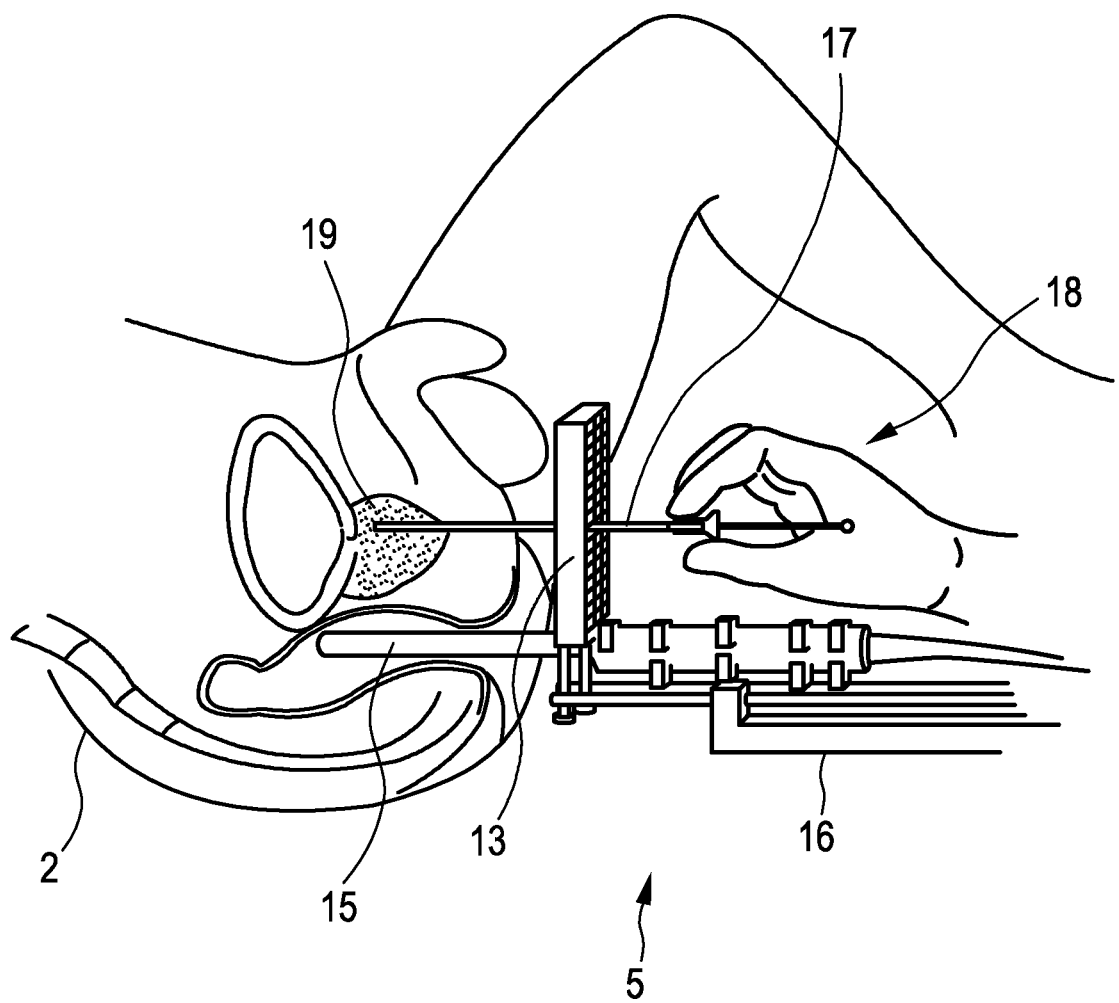
FIG. 2 shows schematically and exemplarily elements of the brachytherapy system shown in FIG. 1 in more detail.

The placing unit 5 comprises an introduction element 17 for introducing the several groups of brachytherapy seeds consecutively into the person 2 in accordance with a treatment plan. In this embodiment the introduction element 17 is a catheter. The several groups of brachytherapy seeds can be manually introduced into the person 2 by using a grid template 13. In FIG. 2 reference number 18 indicates a hand of an operator like a physician introducing brachytherapy seeds into the person 2 by using the catheter 17. The placing unit 5 further comprises an ultrasound probe 15, which is connected to an ultrasound control unit 7, for generating an ultrasound image of the person 2. The ultrasound probe 15 and the grid template 13 are both attached to a holding element 16. The ultrasound probe 15 is preferentially a transrectal ultrasound (TRUS) probe. The TRUS probe 15 can be adapted to acquire three-dimensional life images. It can allow for an automatic acquisition of an entire volume without having to mechanically move the TRUS probe 15. However, the ultrasound probe can also be a two-dimensional ultrasound probe, in particular, a biplane two-dimensional TRUS probe, wherein in this case preferentially the ultrasound probe is translated and/or rotated to reconstruct a three-dimensional image. In particular, the ultrasound probe and the ultrasound control unit can be adapted to use beam steering and spatial compounding for forming the three-dimensional image. In the following different techniques for constructing the three-dimensional image will be exemplarily described in more detail.

Figure 3:
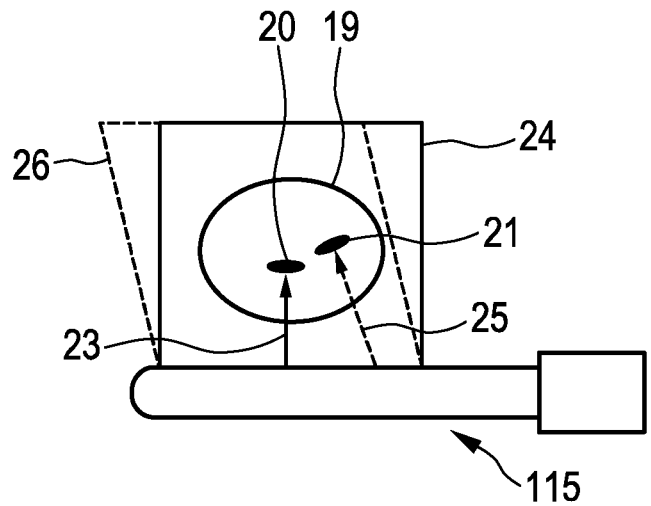
FIGS. 3 to 6 illustrate different ultrasound beam configurations that may be used for ultrasonically imaging brachytherapy seeds within the living being.

FIG. 3 shows schematically and exemplarily two brachytherapy seeds 20, 21, which have been introduced into the prostate 19 of the person 2. The ultrasound probe 115 shown in FIG. 3 has a relatively large size transducer resulting in a field of view 24, 26, which completely covers the prostate 19. FIG. 3 illustrates two acquisition directions, i.e. two directions of the ultrasound beam, a first direction 23 with the corresponding field of view 24 and a second direction 25 with a corresponding field of view 26. In this example the three-dimensional image is generated by compounding images acquired with different beam angles, i.e. acquired in different acquisition directions, without changing the position of the ultrasound probe 115. Each brachytherapy seed 20, 21 within the tissue of the prostate 19 is interrogated by different beam angles.

Figure 4A:
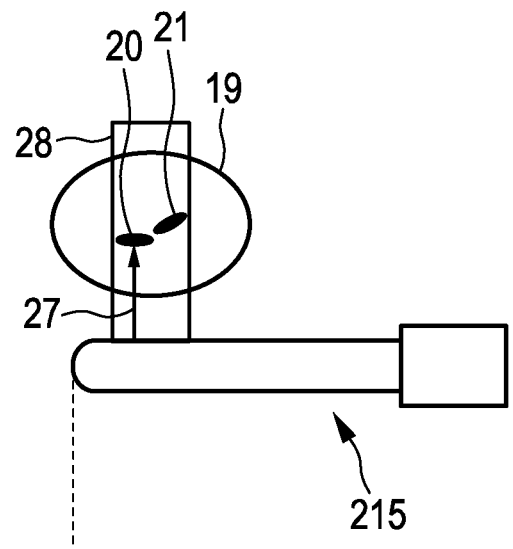
Figure 4B:
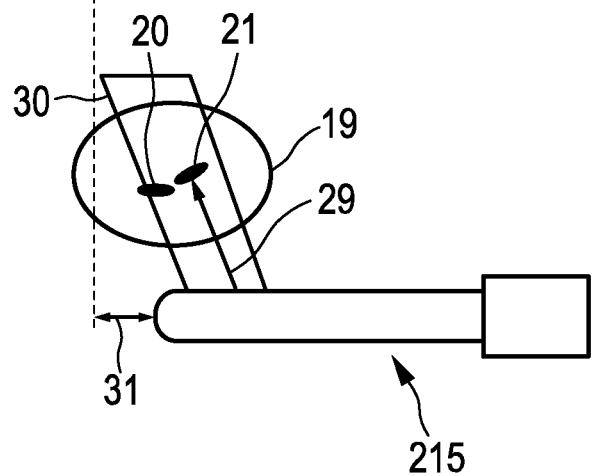

FIGS. 4a and 4b show another embodiment of an ultrasound probe 215, which has a smaller field of view 28, 30. The transducer size and, thus, the field of views 28, 30 are not sufficiently large to cover the whole region of interest, i.e. in this embodiment the complete prostate 19. However, also the ultrasound probe 215 has beam steering capabilities, and the ultrasound probe 215 can be moved relative to the prostate 19 such that a three-dimensional image can be constructed via spatial compounding of different images acquired from different probe positions. In particular, FIG. 4a illustrates the acquisition of a first image by using a first acquisition direction 27 and a corresponding field of view 28 at a first position of the ultrasound probe 215 relative to the prostate 19 and FIG. 4b illustrates the acquisition of a second image in a second acquisition direction 29 by using a corresponding field of view 30 at a second position of the ultrasound probe 215 relative to the prostate 19. The difference with respect to the positions of the ultrasound probe 215 relative to the prostate 19 is indicated in FIG. 4a by the double arrow 31.

In a further example during acquiring the ultrasound images the beam angle may be fixed such that each brachytherapy seed is interrogated by one beam angle only, wherein the probe position may be changed, in order to simulate the effects of beam steering. Desired effects of beam steering, which can be obtained by steering the beam used for generating the ultrasound image or by simulating such a beam steering, will in the following be described with reference to FIGS. 5 and 6.

Figure 5:
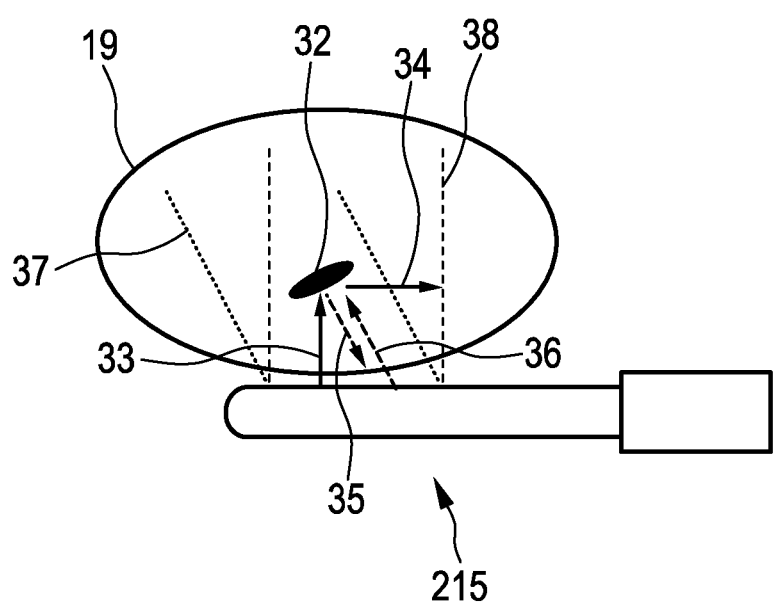

FIG. 5 illustrates the acquisition of an ultrasound image by using the ultrasound probe 215 in a first direction 33 and in a second direction 36. The corresponding fields of view are indicated in FIG. 5 by reference numbers 38 and 37, respectively. The brachytherapy seed 32 primarily reflects the ultrasound wave away from the ultrasound probe 215 in the direction indicated by the arrow 34. The remaining low-intensity echo will generally be obscured by background speckle noise in the acquired image and cannot be seen well in the image. However, by using beam steering the acquisition direction can be changed to the second acquisition direction 35 being substantially perpendicular to the brachytherapy seed 32 such that the ultrasound beam is substantially reflected back towards the ultrasound probe 215 in the direction indicated in FIG. 5 by reference number 35. Thus, by using beam steering the visibility of a brachytherapy seed in an ultrasound image can be increased.

Figure 6:
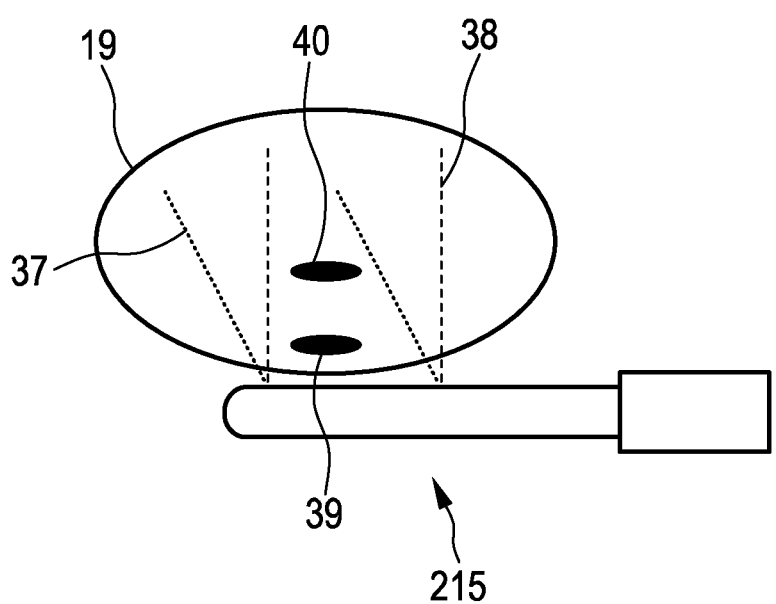

The beam steering technique can also be used to solve a possibly present obstruction problem caused by a brachytherapy seed 40 located in a shadow of another brachytherapy seed 39 as exemplarily shown in FIG. 6. The ultrasound image acquired in a first direction with a corresponding field of view 38 does not clearly show the brachytherapy seed 40, because it is in the shadow of the other brachytherapy seed 39. However, an ultrasound image acquired in a second direction with a corresponding field of view 37 also shows the brachytherapy seed 40 behind the other brachytherapy seed 39. Thus, the brachytherapy seed 40 in the shadow of the other brachytherapy seed 39 is clearly visible in the ultrasound image obtained with a beam angle, which corresponds to the acquisition direction with the field of view 37 in FIG. 6.

The ultrasound probe can be adapted to acquire two-dimensional or three-dimensional ultrasound images, which have been acquired with different beam angles, wherein these two-dimensional or three-dimensional ultrasound images can be compounded to construct a three-dimensional ultrasound image. However, the ultrasound probe and the ultrasound control unit can also be adapted to reconstruct a three-dimensional ultrasound image from several two-dimensional ultrasound images. In particular, the ultrasound probe and the ultrasound control unit can be adapted to construct a three-dimensional image by reconstruction of two-dimensional slices without beam steering.

For instance, the ultrasound probe and the ultrasound control unit can be adapted to generate two-dimensional ultrasound images, which are not compounded, but used to reconstruct a three-dimensional ultrasound image. Moreover, different two-dimensional ultrasound images, which represent different planes within the person 2, which are positioned and/or oriented differently, can be generated and reconstructed to a three-dimensional ultrasound image. Furthermore, the ultrasound probe and the ultrasound control unit can be adapted to generate different compounded two-dimensional ultrasound images, which are reconstructed to a three-dimensional ultrasound image, wherein a two-dimensional compounded ultrasound image can be compounded from several two-dimensional ultrasound images generated with different beam angles. The different two-dimensional compounded ultrasound images can represent different planes within the person 2, which are positioned and/or oriented differently, wherein these two-dimensional compounded ultrasound images can be used for reconstructing the three-dimensional ultrasound image. The ultrasound probe can also be a three-dimensional ultrasound probe directly generating a three-dimensional ultrasound image with or without compounding several three-dimensional ultrasound images. If several three-dimensional ultrasound images are compounded, the several three-dimensional ultrasound images can correspond to different sub-apertures and/or can be associated to different steering angles and/or can be associated to different spatial positions of the three-dimensional ultrasound probe. In the latter case the three-dimensional ultrasound probe may be moved in-between individual volume acquisitions.

Referring again to FIG. 1, the brachytherapy system 14 comprises a display 12 for displaying, for instance, the ultrasound images, determined positions of brachytherapy seeds or of other elements within the person 2. Moreover, the brachytherapy system 14 comprises an electromagnetic tracking unit 6 for electromagnetically tracking the position of the introduction element 17 during the introduction of the groups of brachytherapy seeds into the person 2. The catheter 17, in particular, the tip of the catheter 17, comprises a corresponding electromagnetic element, which can be tracked by the electromagnetic tracking unit 6.

The ultrasound control unit 7 is preferentially adapted to control the generation of the ultrasound image depending on the tracked position of the catheter 17. In particular, if the ultrasound probe comprises a steerable ultrasound beam for generating the ultrasound image, the ultrasound beam is preferentially controlled depending on the tracked position of the catheter 17, in particular, of the tip of the catheter 17. Preferentially, the positions of the brachytherapy seeds, which have actually been introduced into the person 2 by using the catheter 17, are estimated from the tracked positions of the catheter 17 at the respective times of deposition. For instance, the position of a brachytherapy seed relative to the position of the electromagnetic element at the tip of the catheter can be known at the time of deposition and used together with the tracked position of the electromagnetic element for estimating the position of the actually deposited brachytherapy seed. This information, i.e. the approximate position of the actually deposited brachytherapy seed, can be used to control the beam steering of the ultrasound imaging process to exactly locate the seed. Areas far away from the approximate position are preferentially excluded from consideration during the seed detection process. In particular, based on the approximate positions of the brachytherapy seeds, which have already been introduced into the person 2, the ultrasound beam can be steered such that the above described problems of reflections away from the ultrasound probe and of brachytherapy seeds in the shadow of other brachytherapy seeds are reduced, in particular, eliminated. For instance, if the approximate positions of the brachytherapy seeds indicate a situation as schematically and exemplarily shown in FIG. 6, the ultrasound beam of the ultrasound probe can be steered such that at least one of the images, which are compounded for forming the three-dimensional image, corresponds to the acquisition direction with the field of view indicated in FIG. 6 by reference number 37.

The brachytherapy seeds are deposited by inserting the catheter 17 filled with one or several brachytherapy seeds and optionally spacers between several brachytherapy seeds into the person. The one or several brachytherapy seeds should be arranged at locations within the person 2, which are defined in the treatment plan, which may also be regarded as being a dose plan. The electromagnetic tracking unit 6 together with the electromagnetic element at the tip of the catheter 17 can assist in this introduction step by directing the user to the correct locations, wherein the actual location of the catheter 17 at the time of seed deposition can be recorded and provided as an estimation of the seed position to the ultrasound control unit 7 for allowing the ultrasound control unit 7 to perform the ultrasound imaging under consideration of this estimated seed position.

The brachytherapy system 14 further comprises a seed position determining unit 8 for determining the position of a brachytherapy seed depending on the generated three-dimensional ultrasound image. Preferentially, the ultrasound unit formed by one of the above mentioned ultrasound probes and the ultrasound control unit 7 is adapted to generate an ultrasound image, before a group of brachytherapy seeds is introduced into the person 2, and to generate an actual ultrasound image, after the group has been introduced into the person 2, wherein the seed position determining unit 8 is adapted to register the ultrasound images with respect to each other, to generate a subtraction image by subtracting the registered ultrasound images from each other and to determine the position of a brachytherapy seed of the group depending on the generated subtraction image. The registration is preferentially a deformable registration. The determined positions of the one or several brachytherapy seeds of the group are preferentially used for determining desired positions of brachytherapy seeds of further groups, which may be introduced to the person 2.

In particular, for determining the positions of all brachytherapy seeds, which have already been introduced into the person 2, the actual ultrasound image and a previous ultrasound image, which has been acquired after a previous group and before the actual group has been introduced into the person 2, are registered with respect to each other. Thus, the last volume image $I_{n-1}$, which has been acquired before the actual seed deposition, is registered, in particular, elastically and/or deformably registered, with the actual volume image $I_n$, which has been acquired after the actual seed deposition, i.e. a registration transformation $T_{n-1 \to n}$ is calculated. For performing this registration procedure known registration algorithms can be used like the "Demons" algorithm or a variant of this algorithm, which is disclosed, for instance, in the article "Understanding the "Demon's Algorithm": 3D Non-rigid Registration by Gradient Descent" by X. Pennec et al., Medical Image Computing and Computer-Assisted Intervention—MICCAI'99, pages 597 to 606 (1999), which is herewith incorporated by reference. The registered images may then be subtracted from each other for generating a subtraction image. A difference image is therefore created, in which all features present in both images are eliminated, thereby enhancing those features introduced between the two image acquisitions, i.e. thereby enhancing the brachytherapy seeds, which have been introduced into the person 2 during the actual seed deposition. The positions of the brachytherapy seeds of the actually introduced group can then be determined in the subtraction image by using, for instance, known segmentation techniques. This concept of incremental imaging for detecting the position of a most recently implanted brachytherapy seed is illustrated in FIG. 7.

Figure 7:
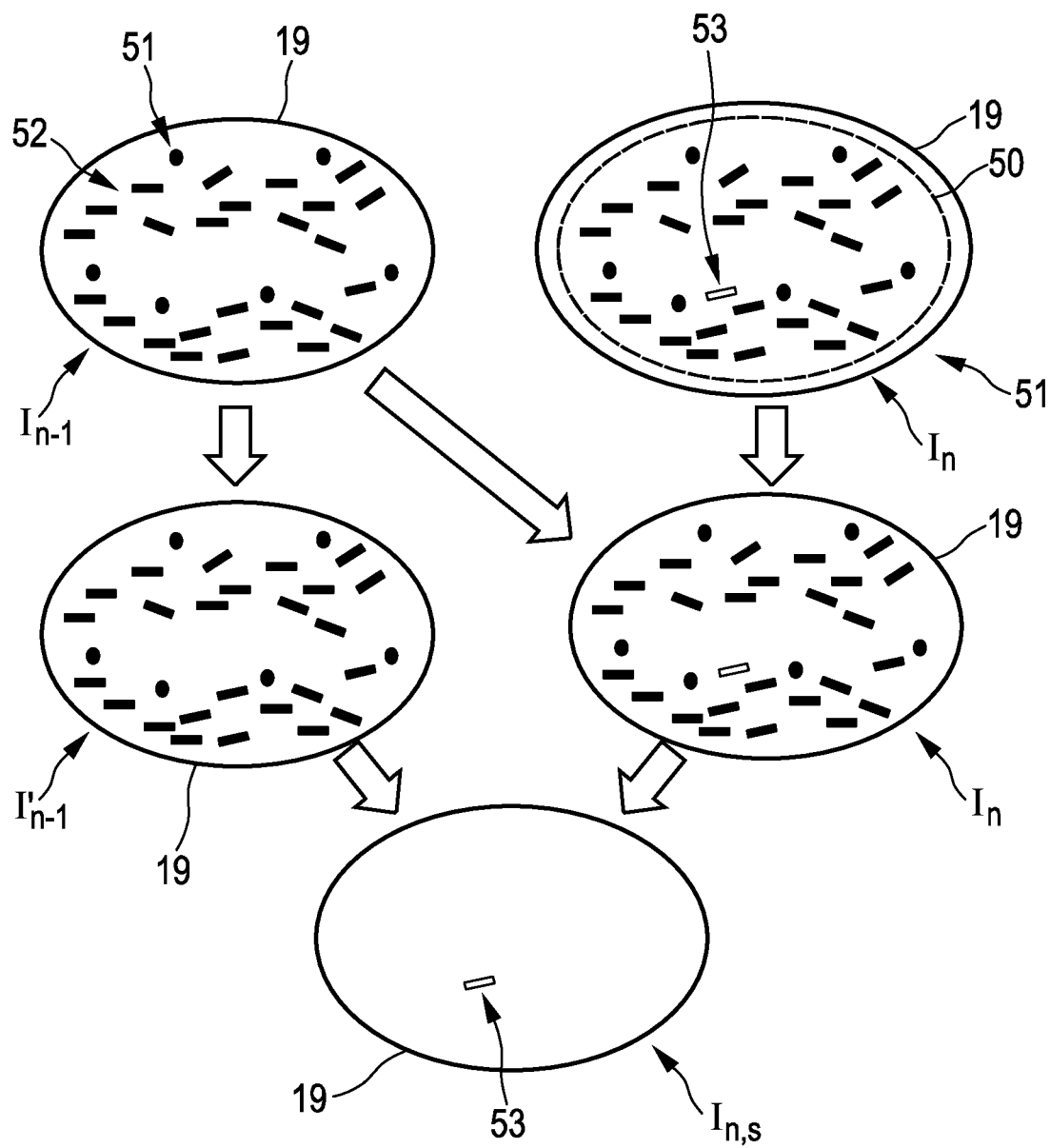
FIG. 7 illustrates generation of a subtraction image.

In FIG. 7 a previous image $I_{n-1}$ shows the brachytherapy seeds 52, which have already been implanted, and microcalcifications 51 within the prostate 19. An actual image $I_n$ also shows the brachytherapy seeds 52 and the microcalcifications 51 visible in the previous image $I_{n-1}$. However, in addition the actual image $I_n$ also shows an actually implanted brachytherapy seed 53. Moreover, the actual image $I_n$ shows an edema of the prostate, which has grown from a previous size indicated by the broken line 50 to an actual size indicated by the solid line 19. In this example the previous image $I_{n-1}$ is deformed to the deformed previous image $I'_{n-1}$ by registering the previous image $I_{n-1}$ with the actual image $I_n$. The deformed previous image $I'_{n-1}$ is then subtracted from the actual image $I_n$ to generate a subtraction image $I_{n,s}$, in which the newly introduced brachytherapy seed 53 is visible in an enhanced way. In another example alternatively or in addition also the previous image $I_{n-1}$ may be deformed during the registration process.

This technique of incremental imaging can prevent erroneous classifications of microcalcifications and other bright image artifacts as brachytherapy seeds. Any seed-like artifact in a base ultrasound image, which has been acquired before the catheter 17 is inserted into the person 2 for the first time and which may also be regarded as being an initial ultrasound image, is generally also visible in subsequent ultrasound images acquired after each insertion of the catheter 17 for introducing a group formed of one or more brachytherapy seeds into the person 2. Since each subsequent ultrasound image is deformably registered to the previous ultrasound image and since subtraction images between successive images are obtained, the seed-like artifacts caused by, for instance, microcalcifications can be cancelled out and not erroneously identified as inserted brachytherapy seeds. Moreover, this incremental technique can at least partly suppress background speckle noise, which will further enhance the visibility of the currently implanted one or several brachytherapy seeds. In addition, by deformably registering images acquired before and after the last insertion of the catheter for introducing the actual group of one or several brachytherapy seeds, the positions of the brachytherapy seeds that were previously implanted at a larger distance from the ultrasound probe can be preserved, even if these previous seeds are located in the shadow of the actually newly implanted brachytherapy seeds, which may be more proximal. Thus, the incremental technique involving incremental imaging and incremental determining of the positions of the brachytherapy seeds can also be used to solve the obstruction problem described above with reference to FIG. 6.

For determining the positions of all brachytherapy seeds introduced into the person 2 the seed position determining unit 8 is further adapted to provide the positions of the brachytherapy seeds of groups, which have already been introduced into the person 2, before the actual group has been introduced, and to combine the actually determined positions and the provided positions for determining the positions of all groups, i.e. of all brachytherapy seeds of all groups, already introduced into the person 2. For instance, newly identified seeds $S_{n,n}$, i.e. the n-th group of new seeds in the coordinate system of the actual image $I_n$, can be stored, wherein these new seeds $S_{n,n}$ can be combined with all prior seeds $S_{total,n-1}$ present in the previous image $I_{n-1}$, wherein the registration transform $T_{n-1 \to n}$ can be applied to the coordinates of the positions of the prior seeds $S_{total,n-1}$, in accordance with following equations:

$$S_{prior,n} = T_{n-1 \to n} \times S_{total,n-1} \qquad (1)$$

and $$S_{total,n} = S_{prior,n} \cup S_{n,n} \qquad (2)$$

The brachytherapy system 14 further comprises a region of interest determining unit 9 for determining a region of interest to be treated within the person 2 depending on the generated actual ultrasound image, in order to allow for an introduction of further groups also depending on the region of interest, which has been determined based on the actual ultrasound image. The region of interest is, for instance, the prostate or a part of the prostate. In particular, the region of interest may be a tumor region within the prostate. It can be determined by known segmentation techniques based on the actual ultrasound image.

The brachytherapy system 14 further comprises a treatment plan providing unit 10 for providing a treatment plan defining a spatial arrangement of brachytherapy seeds within the person 2, wherein the groups of brachytherapy seeds are introduced into the person 2 by using the catheter 17 in accordance with the treatment plan. A treatment plan updating unit 11 updates the treatment plan based on the determined positions of the brachytherapy seeds of the groups already introduced into the person 2, based on the region of interest, i.e. location and/or shape of the region of interest, determined by using the actual ultrasound image and optionally also based on the location and/or shape of further elements of the person 2 like vessels, organs et cetera, which may also be determined based on the actual ultrasound image.

The provided treatment plan, i.e. the initial treatment plan, depends—inter alia—on the region of interest as shown in the base ultrasound image, which has been acquired, before any group has been introduced into the person 2. The region of interest determining unit 9 can be adapted to generate a registration transformation registering the base ultrasound image and the actual ultrasound image with respect to each other and to update the region of interest shown in the base ultrasound image by using the registration transformation, wherein the treatment plan updating unit 11 can be adapted to update the treatment plan based on the determined positions of the brachytherapy seeds of the groups already introduced into the person 2 and based on this updated region of interest. The registration can also be used to update the location and shape of further elements, which are shown in the base ultrasound image and which may have been used for determining the initial treatment plan, wherein the treatment plan can be updated also based on this updated information. The registration of the actual ultrasound image with the base ultrasound image can be a direct registration, wherein the actual ultrasound image is directly registered with the base ultrasound image or an indirect or incremental registration, wherein the base ultrasound image and the subsequently consecutively acquired ultrasound images are pair wise registered with respect to each other, thereby forming a sequence of incremental registrations defining a registration transformation between the base ultrasound image and the actual ultrasound image. The treatment plan, which may also be regarded as being a dose plan, defines at which positions the brachytherapy seeds should be placed. The treatment plan preferentially further defines the radiation dose that the respective brachytherapy seed should apply to the person.

For determining the initial treatment plan different elements shown in the base ultrasound image are preferentially segmented. For instance, the prostate or a part of the prostate forming the region of interest, the rectum, the urethra, the bladder, et cetera are segmented, wherein the initial treatment plan is preferentially determined such that a prescribed target dose is applied to the region of interest, while keeping the radiation dose applied to the other structures minimal. The segmentation procedure and/or the determination of the treatment plan based on the resulting segmentations can be performed manually, semi-automatically or completely automatically.

The registration transformation $T_{n-1 \to n}$ can also be used to update the segmentations, in particular, the shapes and locations of all segmentations from the previous ultrasound image to the actual ultrasound image, wherein based on these updated segmentations and all locations of already placed brachytherapy seeds $S_{total,n}$ the treatment plan updating unit 11 can update the treatment plan. Preferentially, the treatment plan updating unit 11 takes into account the already delivered radiation dose, which is defined by the positions of the already placed brachytherapy seeds and there dwell times, and the prescribed radiation dose targets. The positions of the brachytherapy seeds that still need to be delivered to achieve the prescribed radiation dose targets are determined based on the already delivered radiation dose. This updating of the treatment plan is preferentially performed each time when an incremental ultrasound image $I_n$ has been acquired. The actual adaptively updated treatment plan may or may not differ from the previously adaptively updated treatment plan. If more brachytherapy seeds are needed according to the latest treatment plan, the brachytherapy seed insertion continues with the (n+1)-th iteration of catheter insertion and imaging. Otherwise the procedure is completed.

Instead of performing incremental registrations $I_{n-1} \to I_n$ all ultrasound images can be registered back to the base line ultrasound image $I_0$. Or, for enhanced consistency between all registration transformations, the registrations can be carried out jointly and simultaneously between $I_{n-1}$ and $I_n$ as well as between $I_n$ and $I_0$. Considering the base ultrasound image $I_0$ during the registration procedure can avoid errors, which may accumulate in successive incremental image registrations.

Figure 8:
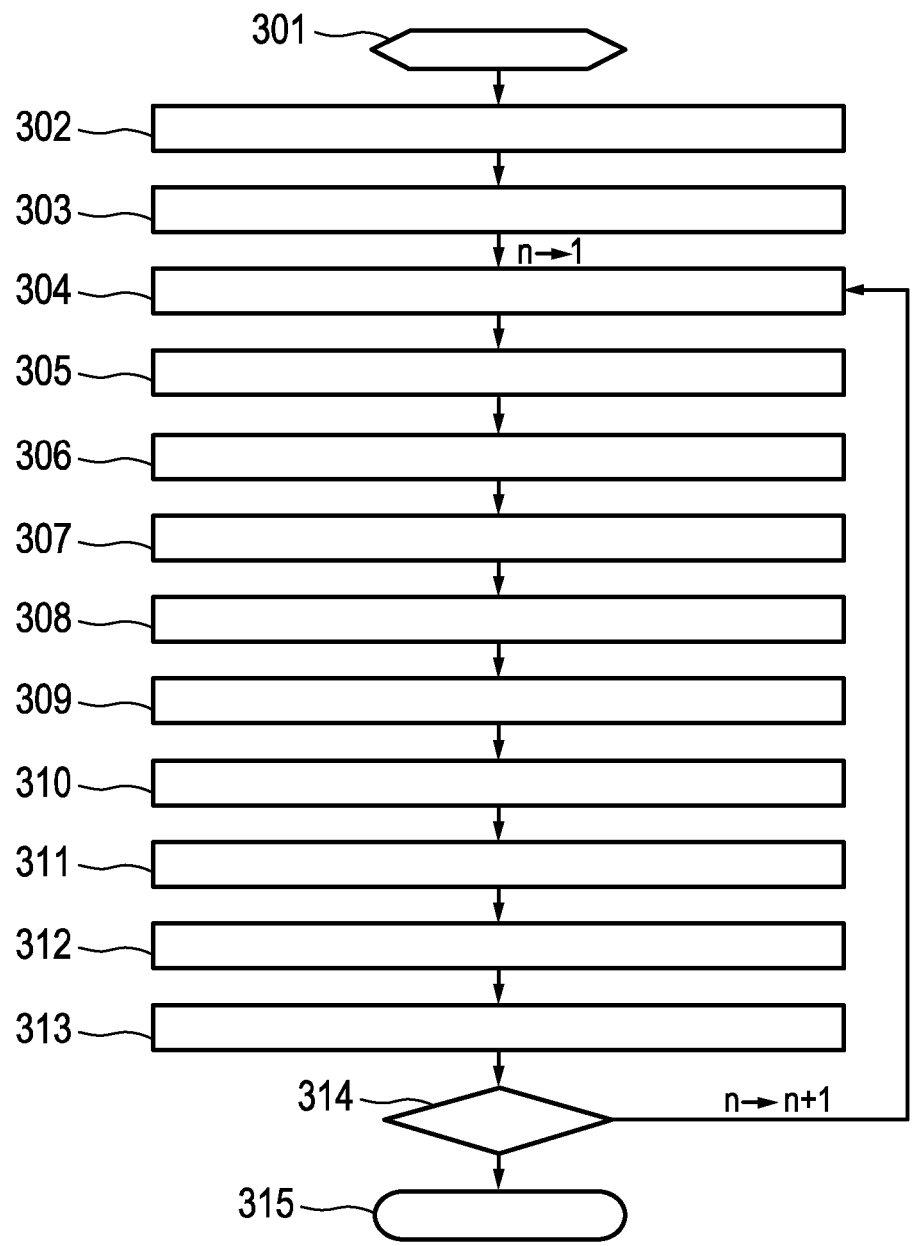
FIGS. 8 and 9 show flowcharts exemplarily illustrating embodiments of a brachytherapy method for applying brachytherapy to a living object.

In the following two embodiments of brachytherapy methods will exemplarily be described with reference to flowcharts shown in FIGS. 8 and 9. A first embodiment illustrated in FIG. 8 uses incremental image registration and a second embodiment illustrated in FIG. 9 uses a registration with the base ultrasound image, wherein the registrations are used to keep track of segmentations, in particular, of organ segmentations, and all seed locations, i.e. all seed positions, throughout the insertion procedure.

After the brachytherapy method has started in step 301, in step 302 an initial three-dimensional TRUS volume, i.e. the base ultrasound image $I_0$, is acquired. In step 303 segmentations are created in the base ultrasound image $I_0$ and an initial treatment plan is determined based on the created segmentations and prescribed radiation dose targets. In step 304 a first group comprising one or several brachytherapy seeds is introduced into the person 2 by using an introduction element like a catheter or a needle in accordance with the treatment plan, wherein the position of the introduction element is electromagnetically tracked during the introduction of the actual group into the person, especially at the time of depositing the one or several brachytherapy seeds of the actual group. After the group has been deposited, the introduction element is retracted from the person. Then, in step 305 the n-th intra-procedure three-dimensional TRUS volume $I_n$ is acquired, wherein during the first iteration n is 1. During the acquisition of the intra-procedure three-dimensional TRUS volume $I_n$ the ultrasound image generation is controlled depending on the position of the introduction element during the introduction procedure tracked in step 304. In step 306 the actual image $I_n$ acquired in step 305 is registered with the previous image $I_{n-1}$ for generating a registration transformation $T_{n-1 \to n}$. The registered images are subtracted from each other to create an n-th subtraction image $I_{n,s}$, in step 307. In step 308 new brachytherapy seeds are detected in the subtraction image $I_{n,s}$. In step 309 the registration transformation $T_{n-1 \to n}$ is used to update prior seed locations for the actual ultrasound image $I_n$, wherein in step 310 the new and prior brachytherapy seeds, i.e. the new and prior brachytherapy seed positions, are combined in the coordinate system of the actual ultrasound image $I_n$. In step 311 the registration transformation $T_{n-1 \to n}$ is used to update the segmentations, and in step 312 the delivered radiation dose, i.e. the radiation dose delivered by the new brachytherapy seeds and the prior brachytherapy seeds, is calculated. In step 313 the treatment plan for placing the remaining brachytherapy seeds is updated. In step 314 it is determined whether further brachytherapy seeds need to be deposited. If this is the case, the method continues with step 304. Otherwise the method ends with step 315.

Figure 9:
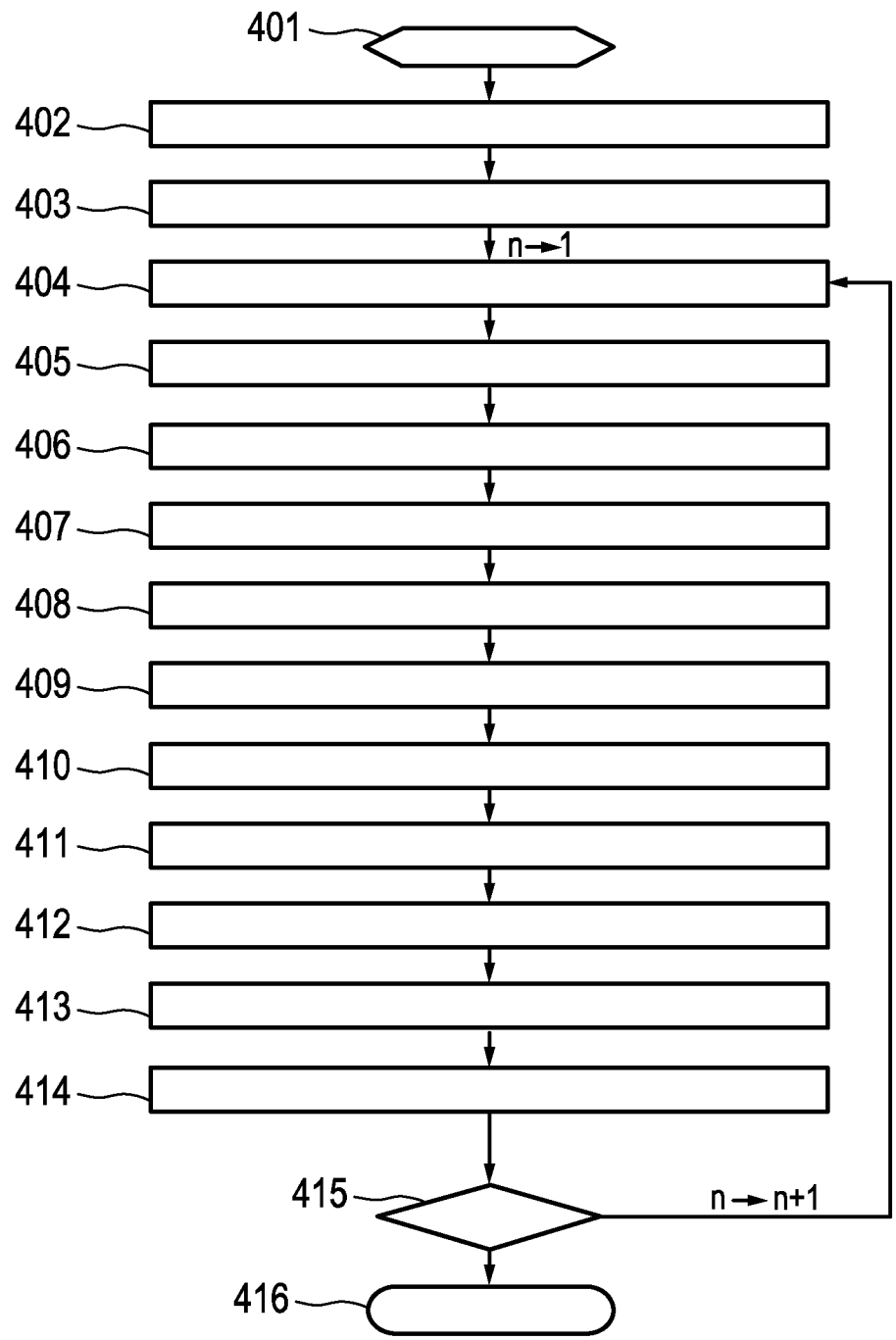

Steps 401 to 408 of the second embodiment of the brachytherapy method illustrated in FIG. 9 are similar to steps 301 to 308 described above with reference to FIG. 8. Moreover, in step 409 the actual ultrasound image $I_n$ is registered with the base ultrasound image $I_0$ for finding a registration transformation $T_{0 \to n}$. In step 410 the transformation $T_{0 \to n}$ is used to bring the previous seed positions from a coordinate system defined by $I_0$ to a coordinate system defined by $I_n$. In step 411 the registration transformation $T_{0 \to n}$ is used to update the segmentations and in step 412 an inverse region transformation $T_{n \to 0}$ is calculated and used to transform the new seed positions to the coordinate system of $I_0$. The remaining steps 413 to 416 correspond to steps 312 to 315 described above with reference to FIG. 8.

Some steps of the brachytherapy method described above with reference to FIGS. 8 and 9 can be regarded as being steps of an assisting method for assisting in performing a brachytherapy. For instance, the electromagnetic tracking of the position of the introduction element in steps 304 and 404 and steps 305 to 315 and 405 to 416, respectively, can be regarded as being steps of the assisting method. Correspondingly, the electromagnetic tracking unit 6, the ultrasound unit 7, 15, the seed position determining unit 8, the region of interest determining unit 9, the treatment plan providing unit 10, which may just be a storing unit, which stores an already determined initial treatment plan and initial segmentations and which provides the stored treatment plan and the segmentations, and the treatment plan updating unit 11 may be regarded as forming an assisting apparatus 1 for assisting in performing a brachytherapy.

By updating the segmentations also a swelling of the object, in which the introduction element is inserted, in particular, of a prostate, can be considered, while inserting the remaining brachytherapy seeds. In particular, the volume of the prostate generally increases during the treatment procedure as a result of the trauma caused by inserting the introduction element. The deformable registration of images acquired over time enables the brachytherapy system to measure prostate swelling and adapt the treatment plan to compensate for the larger volume of the prostate. The deformable registration can therefore also be used to detect and measure edema.

LDR brachytherapy can be used to treat prostate cancer in early stages and entails a permanent placement of radioactive brachytherapy seeds inside the prostate to kill the cancer cells via radiation. The positions of these brachytherapy seeds are accurately planned preoperatively to ensure a sufficient coverage of the target gland while sparing organs at risk such as the urethra and the rectum. An accurate placement of the brachytherapy seeds leads to a better treatment outcome and less toxicity. However, in known brachytherapy systems deviations from the plan are generally present due to problems such as prostate motion and deformation caused by needle or catheter insertion, prostate edema, needle or catheter bending, et cetera. Prostate swelling caused by the trauma of needle or catheter insertion is a major source of error as the enlargement of the prostate is not taken into account in the initial treatment plan.

The brachytherapy system described above with reference to, for instance, FIG. 1 provides therefore preferentially a dynamic dosimetry and planning technique, which entails an accurate and real-time localization of already implanted brachytherapy seeds and a modification of planned positions and of the number of remaining brachytherapy seeds, in order to cover up under radiated regions and avoid over radiating organs at risk. The brachytherapy system is particularly adapted to circumvent following obstacles in seed detection by using ultrasound: a) the creation of a shadow in the ultrasound image by highly echogenic seeds that can obstruct other seeds located in the shadow area, b) dispersing an incoming ultrasound wave by a seed away from the ultrasound probe such that the seed appears less bright and is sparely distinguishable from background speckle and c) seed-like image artifacts caused by, for instance, microcalcifications in the prostate. For circumventing these obstacles the brachytherapy system is preferentially adapted to perform incremental imaging, which is combined with beam steering and elastic deformable registration. Since the brachytherapy seeds are implanted sequentially, real-time dosimetry and planning can allow the physician to modify the positions and number of remaining brachytherapy seeds, intra-operatively, to compensate for possible errors.

Incremental imaging is preferentially used to identify the positions of newly implanted brachytherapy seeds, as the brachytherapy seeds are implanted sequentially. The brachytherapy system may be adapted to take a three-dimensional image of, for instance, the prostate before and after each brachytherapy seed deposition or before and after the deposition of all brachytherapy seeds within one needle or catheter. A group of brachytherapy seeds may be defined by a single brachytherapy seed only or by several brachytherapy seeds, wherein the several brachytherapy seeds may be brachytherapy seeds within one needle or catheter. The three-dimensional image taken before and after the respective brachytherapy seed deposition may be produced by spatially compounding several two-dimensional or three-dimensional images acquired at different beam angles.

The electromagnetic tracking of the introduction element, in particular, of the tip of the introduction element, at the time of depositing the respective brachytherapy seed, leads to an estimated position of the brachytherapy seed. This estimated position can be used to narrow down the search area, when identifying the brachytherapy seed in the subtraction image as described above with reference to, for instance, FIG. 7.

Although in above described embodiments the brachytherapy is mainly applied to the prostate, the brachytherapy can also be applied to other parts, in particular, to other organs, of a human being or an animal.

Although in above described embodiments the tracking is performed by using electromagnetic tracking The tracking unit can also be adapted to use another tracking technique for tracking the position of the introduction element like fiber optical shape sensing tracking.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of a registration transformation, the segmentation procedures, the updating procedures, et cetera performed by one or several units or devices can be performed by any other number of units or devices. For example, steps 306 to 313 and 406 to 414 can be performed by a single unit or by any other number of different units. The procedures and/or the control of the assisting apparatus in accordance with the assisting method and/or the control of the brachytherapy system in accordance with the brachytherapy method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an assisting apparatus for assisting in performing brachytherapy. The position of an introduction element like a catheter is tracked particularly by using electromagnetic tracking, while a group of seeds is introduced into a living object. This provides a rough knowledge about the position of the seeds within the object. An ultrasound image showing the group is generated depending on the tracked position of the introduction element and, thus, depending on the rough knowledge about the position of the seeds, in order to optimize the ultrasound visualization with respect to showing the introduced seeds. Based on this optimized ultrasound visualization the position of a seed of the group is determined, thereby allowing for an improved determination of seed positions and correspondingly for an improved brachytherapy performed based on the determined positions.

The invention claimed is:

1. An assisting apparatus for assisting in performing brachytherapy, during which a brachytherapy seed group including at least one brachytherapy seed is introduced into a living object by using an introduction element, the apparatus comprising:
   an electromagnetic tracking unit for tracking the position of the introduction element during the introduction of the group into the living object,
   an ultrasound unit for generating an ultrasound image of the living object, wherein the ultrasound image shows the group within the living object, wherein the generation of the ultrasound image is controlled depending on the tracked position of the introduction element, and
   a seed position determining unit for determining the position of a brachytherapy seed of the group depending on the generated ultrasound image.

2. The assisting apparatus as defined in claim 1, wherein the ultrasound unit is adapted to generate an ultrasound image, before the group is introduced into the living object, and an actual ultrasound image, after the group has been introduced into the living object, wherein the seed position determining unit is adapted to register the ultrasound images with respect to each other, to generate a subtraction image by subtracting the registered ultrasound images from each other and to determine the position of a brachytherapy seed of the group depending on the generated subtraction image.

3. The assisting apparatus as defined in claim 1, wherein several groups of brachytherapy seeds are consecutively introduced into the living object by using the introduction element, wherein each group includes at least one brachytherapy seed, the ultrasound unit is adapted to generate an actual ultrasound image, after a group has been introduced into the living object, wherein the seed position determining unit is adapted to determine the positions of brachytherapy seeds of groups already introduced into the living object depending on the generated actual ultrasound image, in order to allow for an introduction of further groups depending on the positions of the brachytherapy seeds of groups already introduced.

4. The assisting apparatus as defined in claim 3, wherein the seed position determining unit is adapted to:
   register the actual ultrasound image and a previous ultrasound image, which has been acquired after a previous group and before the actual group has been introduced, with respect to each other,
   generate a subtraction image by subtracting the registered ultrasound images from each other,
   determine the positions of the brachytherapy seeds of the actually introduced group depending on the subtraction image,
   provide the positions of the brachytherapy seeds of groups having been introduced into the living object before the actual group has been introduced,
   combine the actually determined positions and the provided positions for determining the positions of all groups already introduced into the living object.

5. The assisting apparatus as defined in claim 3, wherein the apparatus further comprises a region of interest determining unit for determining a region of interest to be treated within the living object depending on the generated actual ultrasound image, in order to allow for an introduction of further groups also depending on the region of interest determined depending on the actual ultrasound image.

6. The assisting apparatus as defined in claim 3, wherein the apparatus further comprises:
 a treatment plan providing unit for providing a treatment plan defining a spatial arrangement of brachytherapy seeds within the living object, wherein the introduction element is adapted to introduce the groups in accordance with the treatment plan,
 a treatment plan updating unit for updating the treatment plan based on the determined positions of the brachytherapy seeds of the groups already introduced into the living object, wherein the introduction element is adapted to introduce further groups depending on the updated treatment plan.

7. The assisting apparatus as defined in claim 6, wherein the apparatus comprises a region of interest determining unit for determining a region of interest to be treated within the living object depending on the generated actual ultrasound image, wherein the treatment plan updating unit is adapted to update the treatment plan also based on the determined region of interest.

8. The assisting apparatus as defined in claim 7, wherein the provided treatment plan depends on a region of interest, which is shown in a base ultrasound image and which is to be treated by the brachytherapy seeds, wherein the base ultrasound image has been acquired, before any group has been introduced into the living object, wherein the region of interest determining unit is adapted to generate a registration transformation registering the base ultrasound image and the actual ultrasound image with respect to each other and to update the region of interest shown in the base ultrasound image by using the registration transformation, wherein the treatment plan updating unit is adapted to update the treatment plan based on the determined positions of the brachytherapy seeds of the groups already introduced into the living object and based on the updated region of interest.

9. The assisting apparatus as defined in claim 1, wherein the ultrasound unit is adapted to use a steerable ultrasound beam for generating the ultrasound image, wherein the ultrasound beam is controlled depending on the tracked position of the introduction element.

10. The assisting apparatus as defined in claim 1, wherein the ultrasound unit is adapted to generate a compound ultrasound image as the ultrasound image by acquiring several ultrasound images which correspond to different ultrasound beam directions and by combining the several ultrasound images.

11. A brachytherapy system for applying brachytherapy to a living object, the brachytherapy system comprising:
 an introduction element for introducing several groups of brachytherapy seeds consecutively into the living object in accordance with the treatment plan, and
 an assisting apparatus for assisting in performing the brachytherapy as defined in claim 1.

12. An assisting method for assisting in performing brachytherapy, during which a brachytherapy seed group including at least one brachytherapy seed is introduced into a living object by using an introduction element, the assisting method comprising:
 tracking the position of the introduction element during the introduction of the group into the living object by an electromagnetic tracking unit,
 generating an ultrasound image of the living object by an ultrasound unit, wherein the ultrasound image shows the group within the living object, wherein the generation of the ultrasound image is controlled depending on the tracked position of the introduction element, and
 determining the position of a brachytherapy seed of the group depending on the generated ultrasound image by a seed position determining unit.

13. A computer program product for assisting in performing brachytherapy, during which a brachytherapy seed group including at least one brachytherapy seed is introduced into a living object by using an introduction element, the computer program product comprising a non-transient computer-readable storage medium having encoded thereon program code causing an assisting apparatus to carry out an assisting method, when the computer program is run on a computer controlling the assisting apparatus, the assisting method comprising:
 tracking the position of the introduction element during the introduction of the group into the living object by an electromagnetic tracking unit,
 generating an ultrasound image of the living object by an ultrasound unit, wherein the ultrasound image shows the group within the living object, wherein the generation of the ultrasound image is controlled depending on the tracked position of the introduction element, and
 determining the position of a brachytherapy seed of the group depending on the generated ultrasound image by a seed position determining unit.

14. An assisting apparatus for assisting in performing brachytherapy, during which a brachytherapy seed group including at least one brachytherapy seed is introduced into a living object by using an introduction element, the apparatus comprising:
 a fiber optical shape sensing tracking unit for tracking the position of the introduction element during the introduction of the group into the living object,
 an ultrasound unit for generating an ultrasound image of the living object, wherein the ultrasound image shows the group within the living object, wherein the generation of the ultrasound image is controlled depending on the tracked position of the introduction element, and
 a seed position determining unit for determining the position of a brachytherapy seed of the group depending on the generated ultrasound image.

* * * * *